United States Patent [19]

Baeumer et al.

[11] Patent Number: 5,238,031
[45] Date of Patent: Aug. 24, 1993

[54] DEVICE FOR INJECTING A FLUID INTO A RECEPTACLE

[75] Inventors: Klaus Baeumer; Juergen Neubert, both of Bonn, Fed. Rep. of Germany

[73] Assignee: Deutsche Forschungsanstalt fur Luft- und Raumfahrt e.V., Cologne, Fed. Rep. of Germany

[21] Appl. No.: 833,528

[22] Filed: Feb. 11, 1992

[30] Foreign Application Priority Data

Feb. 15, 1991 [DE] Fed. Rep. of Germany ....... 4104649

[51] Int. Cl.$^5$ .......................... B65B 31/00; B65B 1/04
[52] U.S. Cl. ......................... 141/27; 141/45; 141/60; 141/121; 141/290; 604/403; 604/416
[58] Field of Search ........................ 141/44, 45, 50, 52, 141/53, 59, 60, 67, 115, 121, 123, , 126, 285, 290, 325, 229, 330, 363, 365, 366, 18, 2, 21-28, 86, 88, 312, 382, 383, 127; 604/403, 411, 414, 416; 222/318, 424

[56] References Cited

U.S. PATENT DOCUMENTS

| | | |
|---|---|---|
| 1,842,134 | 1/1932 | Waite .................. 141/285 |
| 2,807,288 | 9/1957 | Shea .................... 141/18 |
| 3,000,540 | 9/1961 | Wheeler ............... 141/330 |
| 4,532,969 | 8/1985 | Kwaan ................. 141/285 |
| 4,564,054 | 1/1986 | Gustavsson ........... 141/329 |

Primary Examiner—Henry J. Recla
Assistant Examiner—Steven O. Douglas
Attorney, Agent, or Firm—Spensley Horn Jubas & Lubitz

[57] ABSTRACT

A receptacle includes a receiving chamber into which an injection fluid is to be injected. An injection unit includes a syringe having a needle adapted to pierce a diaphragm of the receptacle. The injection unit has a second needle [(28)] that may be advanced through a further diaphragm into a return chamber of the receptacle. The second needle is secured to a sliding pipe coupled to the syringe via a coupling means. Both needles are advanced simultaneously into the receptacle. Then, the syringe is ejected by moving the syringe plunger. The liquid volume displaced from the return chamber reaches the rear barrel chamber via the sliding pipe, the volume of the rear barrel chamber increasing by the amount in which the injection fluid has been ejected, subtracting the volume of the plunger rod. The exchange of liquid is supported by the suction effect of the partial vacuum generated by the lowering of the syringe plunger. The fluid of the injection device is sealed tight against the environment. The device is particularly suitable for use under zero gravity conditions, e.g. in space.

9 Claims, 1 Drawing Sheet

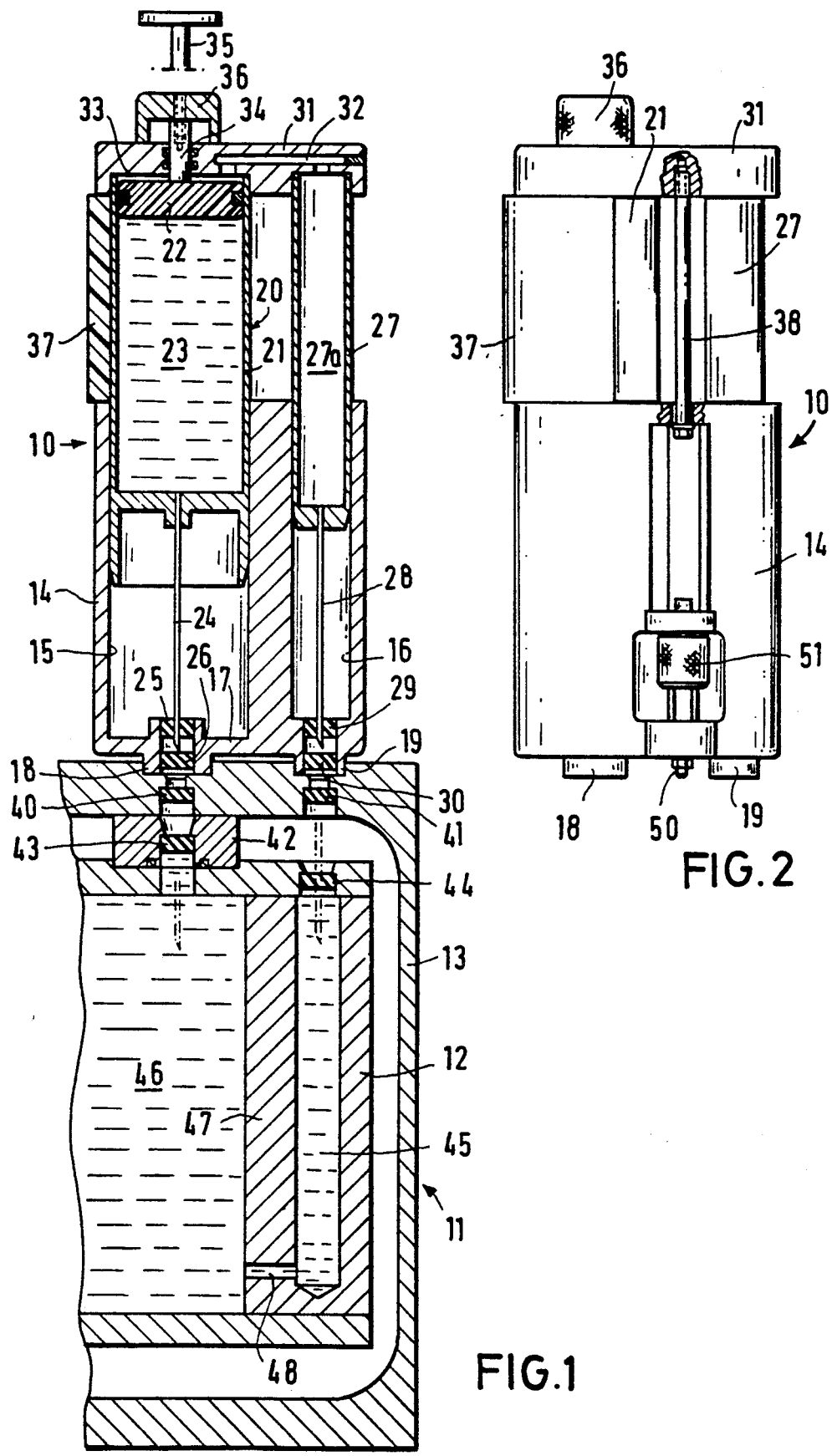

DEVICE FOR INJECTING A FLUID INTO A RECEPTACLE

BACKGROUND OF THE INVENTION

1. Field of the Invention

The invention relates to a device for injecting a fluid into a receptacle filled with fluid, and in particular to a device for an enviromentally neutral and dissipationless exchange of volume between gases and/or liquids under extreme conditions, e.g. in zero gravity in a space laboratory.

2. Description of Related Art

When preserving cells or tissues, a fixing liquid is used. In general, such fixing liquids are toxic so they must not enter the ambient atmosphere. Moreover, a very precise dosing of the fixing liquid is required.

U.S. Pat. No. 4,564,054 describes a transfer device for transferring liquids from a container into a second container closed by a diaphragm, wherein an injection unit with a pair of needles arranged side by side is provided, which are used to pierce the diaphragm simultaneously. One of the needles is connected with a syringe, while, for venting purposes, the other needle communicates with the ambient atmosphere via a filter. When liquid is injected into the second container, air is vented into the environment from this container. Therefore, this system is not suitable for a dissipationless exchange of volume.

It is an object of the present invention to provide a device for injecting a fluid into a receptacle, as well as a receptacle for use with such a device, for a allowing an environmentally neutral and dissipationless exchange of volume in a closed system, while providing for a complete insulation against the environment.

SUMMARY OF THE INVENTION

In accordance with the present invention, this and other objectives are solved by providing an injection unit having a syringe with a first needle for piercing a first diaphragm of the receptacle and, besides that, an overflow chamber that may be filled via a second needle for piercing a second membrane of the receptacle. Thus, the injection unit, on the one hand, allows an injection and, on the other hand, enables the receipt of the fluid displaced from the receptacle with both the injection and the receipt of the displaced fluid being performed in complete insulation against the environment.

A device in accordance with the present invention is particularly suitable for use under zero gravity conditions in a space laboratory. In this case, the receptacle is completely filled with a fluid, preferably a liquid. The liquid displaced from the receptacle is received by the overflow chamber of the fixing unit. A possible implementation of the device of the present invention is the preservation of cells and tissues contained in a liquid in the receptacle by adding a fixing liquid injected in precisely dosed quantities from the injection unit into the receptacle.

The volume of the overflow chamber increases by the same amount by which the volume of the syringe barrel containing the liquid to be injected decreases when the syringe is pushed, subtracting the volume of the plunger rod. The lowering of the syringe plunger causes a partial vacuum behind the same, whereby the exchange of the liquid is supported. This total volume is entirely sealed off from the environment so that neither of the two fliuds can escape into the environment.

Preferably, the injection unit is a separate device that is secured against unintentional actuation prior to its being installed on the receptacle. Both needles are accommodated within the injection unit such that they cannot be accessed from outside. Preferably, they are arranged covered by elastic self-closing partitions (medical septa), generally referred to as diaphragms in the following, and the injection unit may be fixedly mounted to the receptacle or an exterior housing enclosing the same. In order to operate the injection unit, a coupling device connecting the syringe barrel with a sliding pipe is pushed forward, whereby both needles penetrate through the respective diaphragms into the receiving chamber. When the syringe is pressed out thereafter by advancing the syringe plunger, the overflow space taking up the liquid displaced from the receiving chamber increases.

A device in accordance with the present invention is suitable for any kind of dissipationless exchange of volume such as exchanges of gases, of gas and liquid and of liquids. Here, liquids and gases are generally summed up under the term fluids.

A device in accordance with the present invention is particularly designed for use in zero gravity, for example in space laboratories, yet it may also be implemented in the gravity field of the earth or under other gravity conditions.

BRIEF DESCRIPTION OF THE DRAWINGS

The following is a detailed description of an embodiment of the present invention with reference to the accompanying drawings.

In the Figures

FIG. 1 shows a longitudinal section of a device in accordance with the present invention, and FIG. 2 shows a partially cut side elevational view of an injection unit.

DESCRIPTION OF THE PREFERRED EMBODIMENT

The device consists of the injection unit 10 and the receiving unit 11. The receiving unit 11 itself comprises the entirely closed receptacle 12 and the outer housing 13 enclosing the same, the housing also being a container that is sealed germ-tight against the environment.

The injection unit 10 is provided with a guiding means 14 having two parallel guiding bores 15, 16 and two guiding projections 18, 19 provided at its front end wall 17, which may be set into corresponding guiding recesses in the outer housing 13 in a manner excluding interchanging, for mounting the injection unit at a defined position on the receiving unit 11. The guide bores 15, 16 are open to the rear end.

The guide bore 15 has the purpose of guiding the syringe 20 consisting of the syringe barrel 21 and the syringe plunger 22 and containing a liquid 23 within the syringe chamber defined by the syringe plunger 22.

A hollow first needle 24 protrudes from the front end wall of the syringe barrel 21, which ends in the guiding projection 18 when the syringe is drawn back. The guiding projection 18 contains an inner diaphragm 25 and an outer diaphragm 26 defining a cavity. The tip of the hollow needle 24 is within this cavity when the syringe 20 is drawn back.

In the guiding bore 16, the diameter of which is considerably smaller than that of the guiding bore 15, a sliding pipe 27 is guided that is open to the rear end and has the second needle 28 projecting from its front end wall. When the sliding pipe 27 is withdrawn, the front tip of the second needle 28 is within a cavity defined by the two diaphragms 29 and 30 contained in the guiding projection 19.

The open rear ends of the syringe barrel 21 and the sliding pipe 27 are coupled with each other mechanically and in a fluid-tight manner by a coupling means 31. The fluid communication between the interiors of the syringe barrel 21 and the sliding pipe 27 is established by means of a channel 32 extending through the coupling means and communicating the interior 27a of the sliding pipe 27 with the rear barrel chamber 33 of the syringe barrel 21. The coupling means 31 is a cap closing the rear ends of the interior 27a and the rear barrel chamber 33. The plunger rod 34 of the syringe plunger 22 passes through a bore in this cap, the passage being sealed by means of annular seals. An actuator rod 35 may be provided detachably at the plunger rod 34 that may be screwed into the end of the plunger rod, for example, and which has the same diameter as the plunger rod so that it may sealingly slide within the bore of the coupling means. In the state represented in the drawings where the syringe plunger 22 is at the rear end of the syringe barrel 21, a portion of the plunger rod 34 protrudes from the coupling means 31 and instead of the actuator rod 35, a retaining element 36 in the form of a knurled screw is fastened at the rear end of the plunger rod 34, being supported at the exterior of the coupling means 31. By the retaining element 36, the syringe plunger 22 is fixed in the rear end position in the syringe barrel 21.

For fixing the syringe 20 in its rear end position relative to the guiding means 14, a spacer 37 is used, on the one hand, which extends between the rear end of the guiding means 14 and the coupling means 31, and, on the other hand, a holding means 38 in the form of a tie rod is provided that connects the coupling means 31 with the guiding means 14 and restricts the rearward movement of the coupling means 31, yet allows an forward movement from the rear end position.

The outer housing 13 contains a diaphragm 40 axially aligned with the diaphragm 26 and pierceable by the first needle 24, as well as a diaphragm 41 aligned with the diaphragm 30 and pierceable by the second needle 28. Behind the diaphragm 40, there is a filling port 42 of the receptacle 12. This filling port 42 contains a further diaphragm 43. Still another diaphragm 44 is provided in the upper wall of the receptacle in alignment with the diaphragms 29, 30 and 41. This diaphragm 44 may be pierced by the second needle 28.

In axial alignment with the diaphragm 44, a return chamber 45 in the form of a bore is provided in the receptacle 12, being separated from the receiving chamber 46 by a wall 47. The return chamber 45 is connected with the receiving chamber 46 by a passage 48 disposed at the end of the receiving chamber 46 facing away from the filling port 42.

If the injection unit 10 is set onto the receiving unit 11 in the manner depicted in FIG. 1, it is secured to the receiving unit by means of the fastening means 50. The fastening means 50 consists of a threaded screw that may be rotated by turning the actuating means 51 provided in the form of a knurled knob in order to fasten the injection unit 10 to the receiving unit 11 or to detach it therefrom.

The device described above operates as follows: The receiving chmaber 46 and the return chamber 45 are filled with liquid. The front syringe chamber of the syringe barrel 21 is completely filled with a fixing liquid 23. The injection unit 10 is fastened on the receiving unit 11 in the manner shown. The spacer 37 has been removed so that the device is ready for use.

For injecting the liquid 23 into the receiving chamber 46, the coupling means 31 is advanced towards the receiving unit 11. In doing so, the points of the needles 24 and 28 penetrate the outer diaphragms 26 and 30 of the guiding means 14, being guided by the inner diaphragms 25 and 29. The points of the two needles then simultaneously pierce the diaphragms 40 and 41 of the outer housing 13 and upon further pushing, first, the first needle 24 penetrates the diaphragm 43 of the receptacle 12 and then, the second needle 28 penetrates the diaphragm 44 of the receptacle.

The retaining element 36 has been removed and has been replaced with the actuating rod 35. By pushing the actuating rod 35 forward, the syringe plunger 22 is advanced within the syringe barrel 21, whereby liquid 23 is injected into the receiving chamber 46 through the first needle 24. Liquid is displaced from the receiving chamber 46 into the return chamber 45 through the passage 48, and from there, the displaced liquid reaches the interior 27a of the sliding pipe 27 via the second needle 28 and, finally, gets into the rear barrel chamber 33 through the channel 32. The rear barrel chamber 33 expands in the same extent in which liquid is displaced from the front barrel chamber.

The guiding bores 15 and 16 are slightly wider than the outer diameters of the syringe barrel 21 and the sliding pipe 27 so that air contained in the guiding bores may escape when the coupling means 31 is advanced.

The interior 27a of the sliding pipe 27 may contain either a gas (air) or a liquid. Since the volume of this interior 27a is constant, it will not change the sum of volumes when the syringe 20 is pressed out. It is essential that the rear barrel chamber 33 provides an additional volume when the syringe plunger 22 is advanced that is substantially equal to the injected volume of liquid 23.

When the injection is finished, the needles are again withdrawn into the guiding means 14 of the injection unit 10 by withdrawing the coupling menas 31, the tips of the needles 24 and 28 first being pulled out of the diaphragms 43 and 44, thereby wiping drops from the needle tips. Then, the injection unit 10 is pulled from the receiving unit 11. Upon further withdrawal, the needle tips are again wiped off at the diaphragms 40 and 41 so as to be free of drops. By rotating the actuating means 51, the fastening means 50 is detached. The injection unit 10 is removed from the outer housing 13 and stored.

We claim:

1. A device for injecting a fluid into a fluid filled receptacle, comprising a receptacle
   a first diaphragm and a second diaphragm associated with the receptacle,
   an injection unit comprising a syringe, an environmentally sealed overflow chamber defining a fluid volume, a first needle associated with the syringe and adapted to pierce the first diaphragm, and a second needle in fluid communication with the overflow chamber and adapted to pierce the second diaphragm, the syringe comprising a syringe barrel having a plunger slideably mounted therein and defining a barrel chamber on one side of said plunger and a first fluid volume on the opposite side of said plunger, plunger actuating means for moving said plunger;

coupling means for coupling the syringe and the overflow chamber, and a channel fluidically communicating the barrel chamber and the overflow chamber, said first needle communicating with said first fluid volume, whereby a change in the fluid volume of the syringe due to movement of the plunger causes a substantially equal but opposite change in the fluid volume of the overflow chamber.

2. The device of claim 1, comprising a sliding pipe connected with the syringe barrel and the second needle, the sliding pipe enabling the first needle and the second needle to be moved in common from the injection unit into the receptacle.

3. The device of claim 2, wherein the syringe barrel and the sliding pipe are linearly displacable and comprising:

an outer housing enclosing the receptacle, and guide means associated with the injection unit and connectable to the receptacle for guiding the linear displacement of the syringe barrel and the sliding pipe.

4. The device of claim 3, comprising a detachable spacer for preventing relative movement of the syringe and the guide means.

5. The device of claim 3, wherein the guide means defines a guide bore for the syringe barrel and a guide bore for the sliding pipe, and comprising a first pierceable diaphragm aligned with the first needle for sealing the guide means at a location in the guide means substantially proximal to the outer housing, and a second pierceable diaphragm aligned with the second needle for sealing the guide means at a location in the guide means substantially proximal to the outer housing.

6. The device of claim 1, comprising a receiving unit associated with the receptacle, and a detachable fastening means for connecting the injection unit and the receiving unit.

7. The device of claim 1, wherein the syringe plunger defines a withdrawn position and comprising:

a plunger rod and an actuating rod, the plunger rod being detachably connected with the actuating rod and extending through the coupling means when the syringe plunger is in the withdrawn position, and a retaining element supported at the exterior of the coupling means, the retaining element being fastenable to at least one of the plunger rod and the actuating rod.

8. The device of claim 1 wherein the receptacle comprises:

a receiving chamber, a return chamber, a wall separating the receiving chamber and the return chamber, a diaphragm for sealing the receiving chamber, a diaphragm for sealing the return chamber, the wall comprising a passage for establishing fluid communication between the receiving chamber and the return chamber, the passage being provided at a location in the wall remote from the diaphragm for sealing the receiving chamber and the diaphragm for sealing the return chamber.

9. The device of claim 8, wherein the diaphragm for sealing the receiving chamber and the diaphragm for sealing the return chamber are not co-planar.

* * * * *